United States Patent
Gonzalez et al.

(10) Patent No.: US 8,911,512 B2
(45) Date of Patent: Dec. 16, 2014

(54) USE OF NIR SPECTRA FOR PROPERTY PREDICTION OF BIO-OILS AND FRACTIONS THEREOF

(71) Applicant: KiOR, Inc., Pasadena, TX (US)

(72) Inventors: Jorge Gonzalez, Houston, TX (US); Leslie May, Houston, TX (US); Vicente Sanchez, Houston, TX (US)

(73) Assignee: KiOR, Inc., Passadena, TX (US)

( * ) Notice: Subject to any disclaimer, the term of this patent is extended or adjusted under 35 U.S.C. 154(b) by 147 days.

(21) Appl. No.: 13/623,726

(22) Filed: Sep. 20, 2012

(65) Prior Publication Data

US 2014/0075827 A1    Mar. 20, 2014

(51) Int. Cl.
| | |
|---|---|
| G01N 21/35 | (2014.01) |
| G01N 21/59 | (2006.01) |
| G01N 33/22 | (2006.01) |
| C10L 1/04 | (2006.01) |
| C10L 1/18 | (2006.01) |
| G06F 17/00 | (2006.01) |

(52) U.S. Cl.
CPC . *G01N 21/59* (2013.01); *C10L 1/18* (2013.01); *G06F 17/00* (2013.01); *C10L 1/1802* (2013.01)
USPC .............. 44/307; 44/308; 73/61.56; 73/61.59; 702/30

(58) Field of Classification Search
CPC .. G01N 21/359; G01N 33/28; G01N 33/2829
USPC ......... 44/307, 308, 385, 388; 73/61.56, 61.59
See application file for complete search history.

(56) References Cited

U.S. PATENT DOCUMENTS

| | | |
|---|---|---|
| 4,800,279 A | 1/1989 | Hieftje et al. |
| 4,963,745 A | 10/1990 | Maggard |
| 5,145,785 A | 9/1992 | Maggard et al. |
| 5,349,188 A | 9/1994 | Maggard |
| 5,362,965 A | 11/1994 | Maggard |
| 5,740,073 A | 4/1998 | Bages et al. |
| 5,750,995 A | 5/1998 | Clarke |
| 5,999,255 A | 12/1999 | Dupée et al. |
| 6,161,060 A | 12/2000 | Collins |
| 6,897,071 B2 | 5/2005 | Sonbul |
| 7,404,411 B2 | 7/2008 | Welch et al. |
| 7,420,170 B2 * | 9/2008 | Ramirez-Arizmendi et al. ................. 250/339.08 |
| 7,875,464 B2 * | 1/2011 | Schabron et al. ............. 436/181 |
| 2007/0143037 A1 | 6/2007 | Lundstedt et al. |
| 2008/0272303 A1 | 11/2008 | Chu et al. |
| 2010/0131247 A1 | 5/2010 | Carpenter et al. |
| 2010/0211329 A1 | 8/2010 | Farquharson et al. |
| 2011/0138679 A1 | 6/2011 | Wells et al. |
| 2011/0138681 A1 | 6/2011 | Ramirez Corredores et al. |
| 2012/0117815 A1 * | 5/2012 | Wechsler et al. ................ 34/282 |
| 2013/0067991 A1 * | 3/2013 | Schabron et al. ............. 73/23.37 |
| 2014/0021101 A1 * | 1/2014 | Schabron et al. ............. 208/309 |

OTHER PUBLICATIONS

International Search Report for PCT Application No. PCT/US2013/058047; filed on Sep. 4, 2013; 8 pages.

* cited by examiner

*Primary Examiner* — Ellen McAvoy
(74) *Attorney, Agent, or Firm* — Dunlap Codding, P.C.

(57) ABSTRACT

Disclosed is a method for determining properties of hydrocarbonaceous samples including a component prepared from: 1) the thermo-catalytic conversion of biomass, or 2) the pyrolytic conversion of biomass with subsequent upgrading. The determination of the property(ies) is by use of a near-infrared spectra based correlation.

40 Claims, 15 Drawing Sheets

USE OF NIR SPECTRA FOR PROPERTY PREDICTION OF BIO-OILS AND FRACTIONS THEREOF

FIELD OF THE INVENTION

The present invention relates generally to methods for determining properties of hydrocarbonaceous samples including a component prepared from: 1) the thermo-catalytic conversion of biomass, or 2) the pyrolytic conversion of biomass with subsequent upgrading. More specifically, the invention relates to the use of a near-infrared spectra based correlation to determine such property(ies).

BACKGROUND OF THE INVENTION

With the rising costs and environmental concerns associated with fossil fuels, renewable energy sources have become increasingly important, and in particular, the production of renewable transportation fuels from the conversion of biomass feedstocks. Many different processes have been, and are being, explored for the conversion of biomass to biofuels and/or specialty chemicals. Some of the existing biomass conversion processes include, for example, combustion, gasification, liquefaction, enzymatic conversion, and thermo-catalytic or pyrolytic conversion. Upgraded pyrolytic or upgraded thermo-catalytic bio-oils are of current focus as blendstocks for transportation fuels. The quality of such bio-oils and fractions, as reflected from their measured properties, are critical with regard to eventual blending with conventional fuels. Such properties for the bio-oil or upgraded bio-oil can include viscosity, total acid number (TAN), density, wt % oxygen measured on a dry basis, wt % water, wt % carbon, wt % hydrogen. Fractions from such bio-oil or upgraded bio-oil can include at least some of the properties listed above, and can further include Motor Octane Number, Research Octane Number, and cetane number. These properties are typically measured using standardized analytical techniques, which can be expensive to run. In addition, such tests are typically time consuming, generally taking 30 minutes or more to complete. Due to this delay in acquiring analytical results, it would be extremely difficult to use such standardized analytical techniques to either: 1) control a bio-oil production process (including upgrading) or 2) control a blending process wherein fractions of such bio-oil are blended with conventional fuels.

Accordingly, there remains a need for an improved and efficient method for determining properties of either: 1) a bio-oil produced from a thermo-catalytic or pyrolytic conversion of biomass or 2) a fuel blended from a conventional fuel and a fraction of such bio-oil.

SUMMARY OF THE INVENTION

In accordance with an embodiment of the present invention, a method is provided for determining a property for a hydrocarbonaceous sample comprising a component prepared from the thermo-catalytic or pyrolytic conversion of biomass with subsequent upgrading; and comprises:

a) measuring a model property for each of a plurality of model hydrocarbonaceous materials comprising varying amounts of the component;

b) acquiring a plurality of model absorbances over a near-infrared spectrum for each of the model hydrocarbonaceous materials;

c) correlating the model properties with the plurality of model absorbances to establish a correlation;

d) acquiring a plurality of sample absorbances over the near-infrared spectrum for the hydrocarbonaceous sample; and e) comparing the plurality of sample absorbances to the plurality of model absorbances using the correlation to thereby determine the property for the hydrocarbonaceous sample.

In accordance with another embodiment of the present invention, the hydrocarbonaceous sample, component, and plurality of model hydrocarbonaceous materials can be transportation fuel-range fractions; and the property can be selected from the group consisting of Motor Octane Number, Research Octane Number, cetane number, and density.

In accordance with other embodiments of the present invention, the hydrocarbonaceous sample, component, and plurality of model hydrocarbonaceous materials can be bio-oils prepared from the thermo-catalytic or pyrolytic conversion of biomass, which can contain oxygen in the range of from about 1 wt % to about 50 wt % oxygen, measured on a dry basis, which can also optionally be at least partially dewatered; and the property can be selected from the group consisting of wt % oxygen measured on a dry basis, viscosity, TAN, wt % water, wt % carbon, and density.

In accordance with another embodiment of the present invention, the hydrocarbonaceous sample, component, and plurality of model hydrocarbonaceous materials can be bio-oils prepared from the thermo-catalytic or pyrolytic conversion of biomass, which are at least partially upgraded (such as by deoxygenation); and the property can be selected from the group consisting of wt % hydrogen, viscosity, TAN, and density.

DETAILED DESCRIPTION OF THE INVENTION

Figure 1:
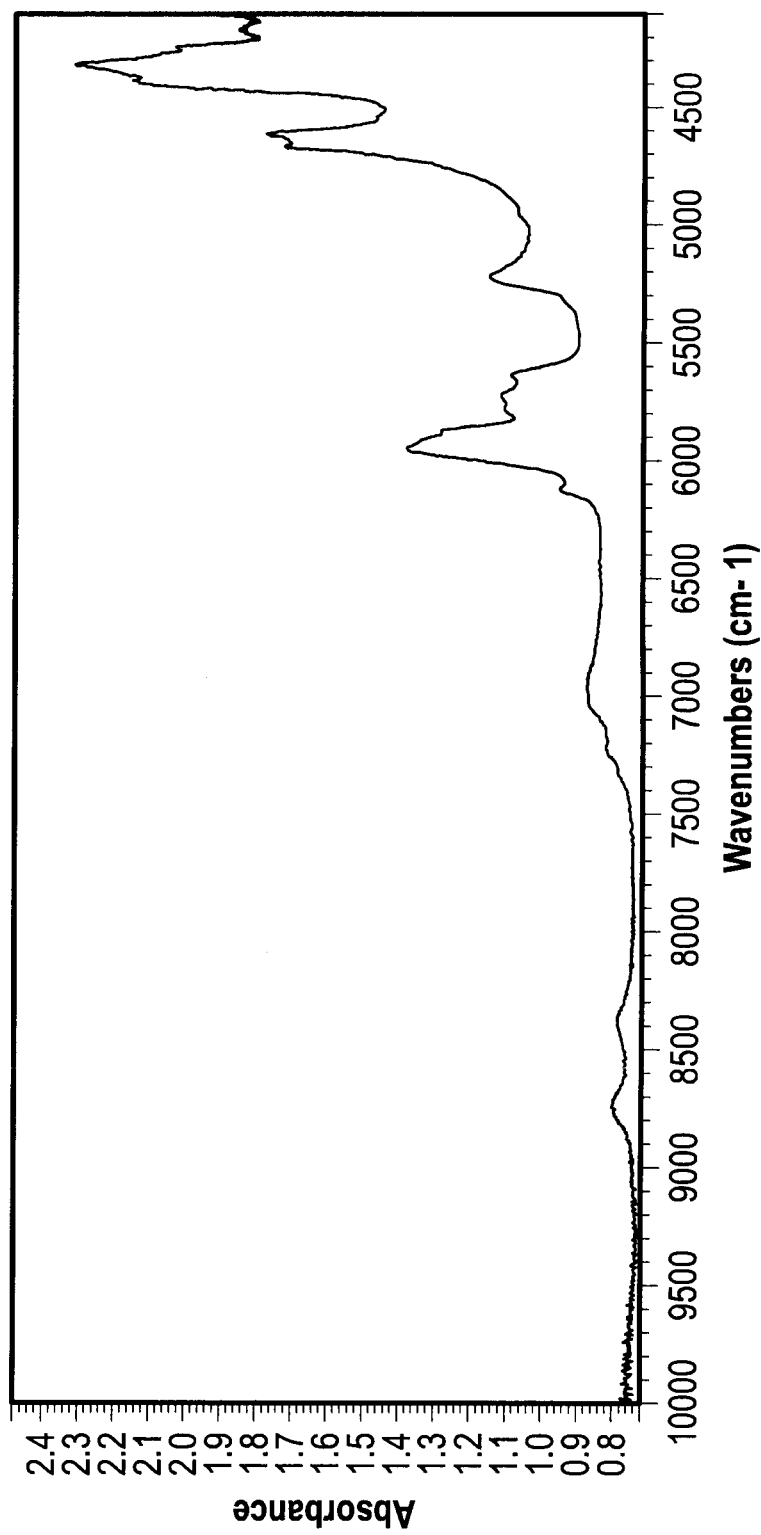
FIG. 1 illustrates a near-infrared spectrum of a typical bio-oil prepared from the thermo-catalytic conversion of biomass.

The biomass material useful in producing the bio-oils used in the current invention can be any biomass capable of being converted to liquid and gaseous hydrocarbons.

Preferred are solid biomass materials comprising a cellulosic material, in particular lignocellulosic materials, because of the abundant availability of such materials, and their low cost. The solid biomass feed can comprise components selected from the group consisting of lignin, cellulose, hemicelluloses, and combinations thereof. Examples of suitable solid biomass materials include forestry wastes, such as wood chips and saw dust; agricultural waste, such as straw, corn stover, sugar cane bagasse, municipal waste, in particular yard waste, paper, and card board; energy crops such as switch grass, coppice, eucalyptus; and aquatic materials such as algae; and the like.

The biomass can be converted at elevated temperatures to form a conversion reactor effluent. In particular, the biomass can be converted in a conversion reactor containing a heat carrier material to thereby produce the conversion reactor effluent comprising vapor conversion products and heat carrier material. The conversion reactor effluent can also include unreacted biomass, coke, or char. The vapor conversion products comprise, consist of, or consist essentially of non-condensable gases including CO and $CO_2$, bio-oil, and water. The conversion reactor can be operated at a temperature in the range of from about 200° C. to about 1000° C., or between about 250° C. and about 800° C., and can be operated in the substantial absence of oxygen. Also, at least a portion of the heat carrier can be a catalyst.

Such catalyst can be any catalyst capable of converting biomass to a bio-oil product having relatively low oxygen levels. The oxygen levels of such bio-oil can be less than about 20 wt % on a dry basis.

More particularly, useful catalysts for the current invention include those containing catalytic acidity and can contain a zeolite. Examples of suitable zeolites include ZSM-5, ZSM-11, ZSM-22, ZSM-23, ZSM-48, mordenite, beta, ferrierite, and zeolite-Y. Additionally, the catalyst may comprise a super acid, including sulfonated, phosphated, or fluorinated forms of zirconia, titania, alumina, silica-alumina, or clays, pillared layered clays and/or silicotitanates or pillared layered silicotitanates. In another embodiment, the catalyst may comprise a solid base including metal oxides, metal hydroxides, and/or metal carbonates. In particular, the oxides, hydroxides, and carbonates of alkali metals, alkaline earth metals, transition metals, and/or rare earth metals are suitable. Other suitable solid bases are layered double hydroxides, mixed metal oxides, hydrotalcite, clays, and/or combinations thereof. In yet another embodiment, the catalyst can also comprise an alumina, such as alpha-alumina.

At least a portion of the vapor conversion products, from either or both of a catalytic or non-catalytic conversion process as described above, can be separated from the conversion reactor effluent, and at least a portion of the vapor conversion products thus separated can be condensed to form a condensate comprising bio-oil and water.

When the heat carrier does not include a catalyst component, the condensate can first be at least partially upgraded, such as by deoxygenation, which can include hydrotreatment, in order to make the resulting upgraded condensate more susceptible to separation. At least a portion of the bio-oil can then be separated from the upgraded condensate, also forming an aqueous phase.

When the heat carrier includes the catalyst as described above, at least a portion of the bio-oil can be separated from the condensate, without the necessity of prior upgrading, also forming an aqueous phase.

In either case, such separation can be by any method capable of separating bio-oil from an aqueous phase, and can include, but is not limited to, centrifugation, membrane separation, gravity separation, and the like. In a specific embodiment, the condensate is separated by gravity separation in a settling vessel into the bio-oil and into the aqueous phase.

The bio-oil can then be upgraded to lower oxygen levels forming an upgraded bio-oil. Such upgrading can be by at least partially deoxygenating and/or hydrotreating the bio-oil. The terms "at least partially deoxygenating" and "at least partially hydrotreated" as used herein includes the removal of at least 80, or at least 90, or at least 95, or at least 99, or at least 100% of the oxygen contained in carbon-hydrogen-oxygen containing compounds, from whatever source, which are subjected to deoxygenation and/or hydrotreatment. Further, products which are at least partially deoxygenated and/or hydrotreated as described herein can comprise less than about 1, or less than about 0.5, or less than about 0.1 wt % oxygen; and/or optionally less than about 5, or less than about 1 ppm sulfur. Any deoxygenation and/or hydrotreatment referred to herein can be accomplished using either a batch or a continuous process.

The upgraded bio-oil can then be fractionated into transportation fuel-range fractions such as bio-naphtha, bio-distillate and bio-jet range blendstocks.

The bio-oil, upgraded bio-oil, and fractions thereof can each be used as a component of the hydrocarbonaceous sample described below.

A method for determining a property for a hydrocarbonaceous sample comprising, consisting of, or consisting essentially of a component prepared from: 1) the thermo-catalytic conversion of biomass, or 2) the pyrolytic conversion of biomass with subsequent upgrading; and comprises, consists of, or consists essentially of:

a) measuring a model property for each of a plurality of model hydrocarbonaceous materials comprising varying amounts of the component;

b) acquiring a plurality of model absorbances over a near-infrared spectrum for each of the model hydrocarbonaceous materials;

c) correlating the model properties with the plurality of model absorbances to establish a correlation;

d) acquiring a plurality of sample absorbances over the near-infrared spectrum for the hydrocarbonaceous sample; and e) comparing the plurality of sample absorbances to the plurality of model absorbances using the correlation to thereby determine the property for the hydrocarbonaceous sample.

The spectra used to acquire the absorbances described above can be fourier transform near-infrared spectra. Also, near-infrared instruments useful in the present invention can be any such instruments capable of producing near-infrared or fourier-transformed near-infrared spectra.

The standard deviation of the wavenumber shift between: 1) a first near-infrared instrument used to acquire an absorbance in steps b) or d), and 2) a second near-infrared instrument can be less than about 0.02, or less than about 0.01 wavenumbers.

In addition, the standard deviation of the wavenumber shift can be sufficient to allow calibration transfer from the first near-infrared instrument to the second near-infrared instrument. The root mean square error of prediction for the second near-infrared instrument can be less than or equal to the root mean square error of prediction for the first near-infrared instrument.

The near infrared spectrum can be sub-divided by wavelength into a plurality of groups, each separately defined by a wavelength range, and each of the absorbances of: 1) the plurality of model absorbances, and 2) the plurality of sample absorbances can be a total absorbance acquired over one of the wavelength ranges corresponding to one of the groups.

Alternatively, a plurality of wavelengths can be identified over the near infrared spectrum, and each of the absorbances of: 1) the plurality of model absorbances, and 2) the plurality of sample absorbances can be an absorbance acquired at one of the plurality of wavelengths.

Fuel Range Fractions

The hydrocarbonaceous sample, component, and plurality of model hydrocarbonaceous materials can each be transportation fuel-range fractions which can be selected from the group consisting of bio-naphtha, bio-distillate and bio-jet range blendstocks. In such case, the property can be selected from the group consisting of Motor Octane Number, Research Octane Number, cetane number, and density.

When the property is Motor Octane Number, the hydrocarbonaceous sample and the plurality of model hydrocarbonaceous materials can have Motor Octane Numbers in the range of from about 70 to about 90, or from about 70 to about 85; and the spectral range for the near-infrared spectrum can be from about 4000 to about 10000 wavenumbers.

When the property is Research Octane Number, the hydrocarbonaceous sample and the plurality of model hydrocarbonaceous materials can have Research Octane Numbers in the range of from about 70 to about 90, or from about 70 to about 85; and the spectral range for the near-infrared spectrum can be from about 4000 to about 10000 wavenumbers.

When the property is cetane number, the hydrocarbonaceous sample and the plurality of model hydrocarbonaceous materials can have cetane numbers in the range of from about 20 to about 60, or from about 20 to about 40; and the spectral range for the near-infrared spectrum can be from about 4000 to about 10000 wavenumbers.

When the property is density, the hydrocarbonaceous sample and the plurality of model hydrocarbonaceous materials can have densities in the range of from about 0.80 to about 0.91, or from about 0.85 to about 0.90 g/ml; and the spectral range for the near-infrared spectrum can be from about 4000 to about 10000 wavenumbers.

The hydrocarbonaceous sample and the plurality of model hydrocarbonaceous materials can further comprise petroleum-sourced fuel components, and can further comprise components selected or obtained from the group consisting of pyrolysis oil, liquefied biomass, hydropyrolysis oils, alcohol, triglyceride-based oil, and combinations thereof.

Such correlations can also be used in processes for blending a petroleum-sourced fuel component with a transportation fuel-range fraction derived from a bio-oil prepared from: 1) the thermo-catalytic conversion of biomass, or 2) the pyrolytic conversion of biomass with subsequent upgrading. Such processes can comprise: a) blending the transportation fuel-range fraction with at least one petroleum-sourced fuel component, b) comparing the value of the property determined from the correlation(s) described above with a desired set point value, and c) adjusting the ratio of the transportation fuel-range fraction to the at least one petroleum-sourced fuel component accordingly.

Raw Bio-Oils

The hydrocarbonaceous sample, component, and plurality of model hydrocarbonaceous materials can each be bio-oils prepared from: 1) the thermo-catalytic conversion of biomass, or 2) the pyrolytic conversion of biomass with subsequent upgrading; wherein such bio-oils can each contain oxygen in the range of from about 1 to about 50, or from about 1 to about 20 wt % oxygen, measured on a dry basis. In such case, the property can be selected from the group consisting of wt % oxygen measured on a dry basis, viscosity, TAN, wt % water, wt % carbon, and density.

When the property is wt % oxygen measured on a dry basis, the spectral range for the near-infrared spectrum can be from about 4000 to about 10000 wavenumbers.

When the property is viscosity, as measured at 40° C., the hydrocarbonaceous sample and the plurality of model hydrocarbonaceous materials can have viscosities greater than 0 and up to about 1200, or from about 10 to about 500 centipoise (cP); and the spectral range for the near-infrared spectrum can be from about 4400 to about 9200 wavenumbers.

When the property is TAN, the hydrocarbonaceous sample and the plurality of model hydrocarbonaceous materials can have TAN values in the range of from about 0.05 to about 50, or from about 5 to about 15 mg KOH/g oil; and the spectral range for the near-infrared spectrum can be from about 4400 to about 9200 wavenumbers.

When the property is wt % water, the hydrocarbonaceous sample and the plurality of model hydrocarbonaceous materials can have wt % water contents in the range of from about 0.2 to about 36, or from about 1 to about 7 wt %; and the spectral range for the near-infrared spectrum can be from about 4400 to about 10000 wavenumbers.

When the property is wt % carbon, the hydrocarbonaceous sample and the plurality of model hydrocarbonaceous materials can have wt % carbon contents in the range of from about 70 to about 82, or from about 74 to about 78 wt %; and the spectral range for the near-infrared spectrum can be from about 4400 to about 9200 wavenumbers.

When the property is density, the hydrocarbonaceous sample and the plurality of model hydrocarbonaceous materials can have densities in the range of from about 1 to about 1.2, or from about 1.05 to about 1.1 g/ml; and the spectral range for the near-infrared spectrum can be from about 4000 to about 10000 wavenumbers.

The hydrocarbonaceous sample and the plurality of model hydrocarbonaceous materials can contain or be selected from the group consisting of pyrolysis oil, liquefied biomass, hydropyrolysis oil, thermo-catalytic oil, and combinations thereof.

Such correlations can be used in processes for producing a bio-oil, under bio-oil production conditions, by: 1) the thermo-catalytic conversion of biomass, or 2) the pyrolytic conversion of biomass with subsequent upgrading. Such processes can comprise: a) comparing the value of the property determined from the correlation(s) described above with a desired set point value, and b) adjusting the bio-oil production conditions accordingly. Such bio-oil production conditions include those described above.

De-Watered Bio-Oils

The hydrocarbonaceous sample, component, and plurality of model hydrocarbonaceous materials can be bio-oils prepared from: 1) the thermo-catalytic conversion of biomass, or 2) the pyrolytic conversion of biomass with subsequent upgrading; wherein the resulting bio-oils are then at least partially de-watered. Such de-watering can be by first "flipping" the layers of the bio-oil by altering the density of either the organic phase or the aqueous phase, such that the organic phase (bio-oil) settles on top. The flipped organic phase can then be separated from the aqueous phase by gravity separation and decanting. Solid material present in the raw bio-oils will tend to concentrate in the aqueous phase, resulting in a significant reduction of the solids content in the resulting organic phase. The thus acquired organic phase can then be subjected to further water (and associated solids) removal by a process like desalting, forming a de-watered bio-oil. In such case, the property can be wt % water, or wt ppm solids by filtration, or any of the other properties described above for the raw bio-oil.

When the property is wt % water, the hydrocarbonaceous sample and the plurality of model hydrocarbonaceous materials can have wt % water contents in the range of from about 0.5 to about 5 wt %; and the spectral range for the near-infrared spectrum can be from about 4500 to about 10000 wavenumbers.

When the property is wt ppm solids by filtration, the hydrocarbonaceous sample and the plurality of model hydrocarbonaceous materials can have wt ppm solids by filtration in the range of from about 100 to about 1500 wt ppm; and the spectral range for the near-infrared spectrum can be from about 4500 to about 10000 wavenumbers.

Such correlation(s) can be used in processes for at least partially de-watering a bio-oil prepared from: 1) the thermo-catalytic conversion of biomass, or 2) the pyrolytic conversion of biomass with subsequent upgrading. Such processes can comprise: a) subjecting the bio-oil to a voltage differential in a desalter operated under desalting conditions, b) comparing the value of the property determined from correlation(s) described above with a desired set point value, and c) adjusting the voltage differential and/or other desalting conditions accordingly. Such other conditions can include, but are not limited to, additive type or quantity added to the raw bio-oil, desalter feed rate, etc. . . . . .

Upgraded Bio-Oils

The hydrocarbonaceous sample, component, and plurality of model hydrocarbonaceous materials can be bio-oils prepared from: 1) the thermo-catalytic conversion of biomass, or 2) the pyrolytic conversion of biomass with subsequent upgrading; wherein the resulting bio-oils are then further upgraded, as described above for the raw bio-oils and de-watered bio-oils. Such upgrading can be an at least partial hydrotreatment of the bio-oils. In such case, the property can be selected from the group consisting of wt % hydrogen and TAN.

When the property is wt % hydrogen, the hydrocarbonaceous sample and the plurality of model hydrocarbonaceous materials can have wt % hydrogen contents in the range of from about 10 to about 14, or from about 11.8 to about 13 wt % hydrogen; and the spectral range for the near-infrared spectrum can be from about 4000 to about 10000 wavenumbers.

When the property is TAN, the hydrocarbonaceous sample and the plurality of model hydrocarbonaceous materials can have TANs greater than 0 and up to about 2, or from about 0.01 to about 0.5 mg KOH/g oil; and the spectral range for the near-infrared spectrum can be from about 4000 to about 10000 wavenumbers.

The correlation of the model properties with the plurality of model absorbances described above can have a correlation coefficient greater than about 0.7, or greater than about 0.8, or greater than about 0.9; and the correlation can be by use of partial least squares.

Such correlation(s) can be used in processes for at least partially deoxygenating a bio-oil prepared from: 1) the thermo-catalytic conversion of biomass, or 2) the pyrolytic conversion of biomass with subsequent upgrading. Such processes can comprise: a) contacting the bio-oil with a de-oxygenation catalyst under de-oxygenation conditions, b) comparing the value of the property determined from the correlation(s) described above with a desired set point value, and c) adjusting the de-oxygenation conditions accordingly. Such conditions can include, but are not limited to, upgrader feed rate, hydrogen to feed ratio, reactor temperature and/or pressure, catalyst regeneration severity, etc. . . .

EXAMPLES

In the following examples, several hydrocarbonaceous samples were analyzed for various properties, and near-infrared spectra were also obtained for each sample for correlation with such properties. Unless otherwise noted, all spectra were obtained at a 2 mm transmission pathlength using a SABiR transflectance probe; and with a 2 wavenumber resolution.

FIG. 1 shows a near-infrared spectrum of a typical bio-oil prepared from the thermo-catalytic conversion of southern yellow pine wood chips (having an oxygen content of around 15 wt %).

As can be seen, such spectra are typically composed of broad overtones and combination bands from the fundamental absorbencies of the mid-infrared (baseline effects). For this reason, it is difficult to assign specific bands. In building the calibration curves/models, spectra were processed by conversion to their second derivatives in order to remove the above described baseline effects.

Figure 2:
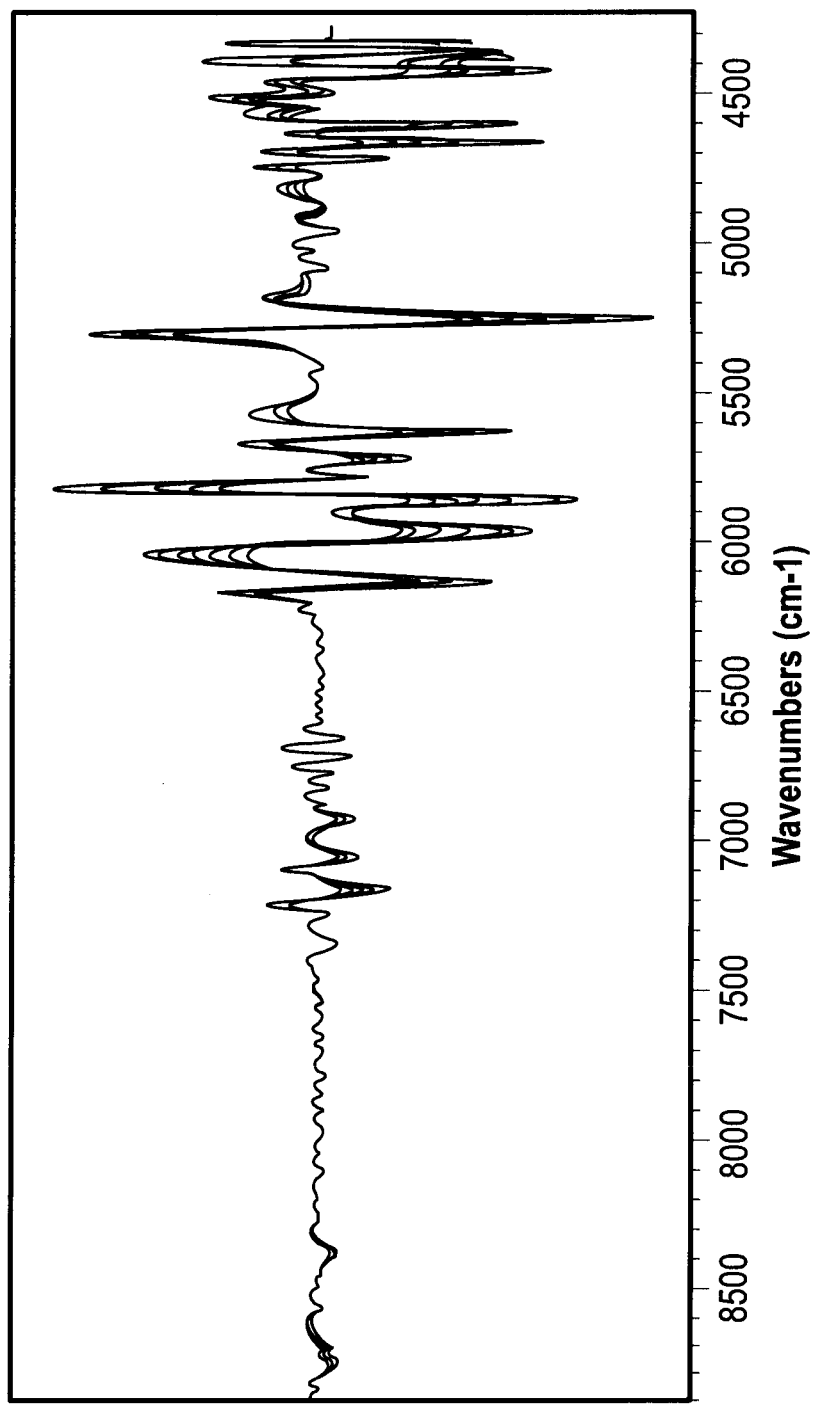
FIG. 2 illustrates a second derivative near-infrared spectra of a typical bio-oil prepared from the thermo-catalytic conversion of biomass.
Figure 3:
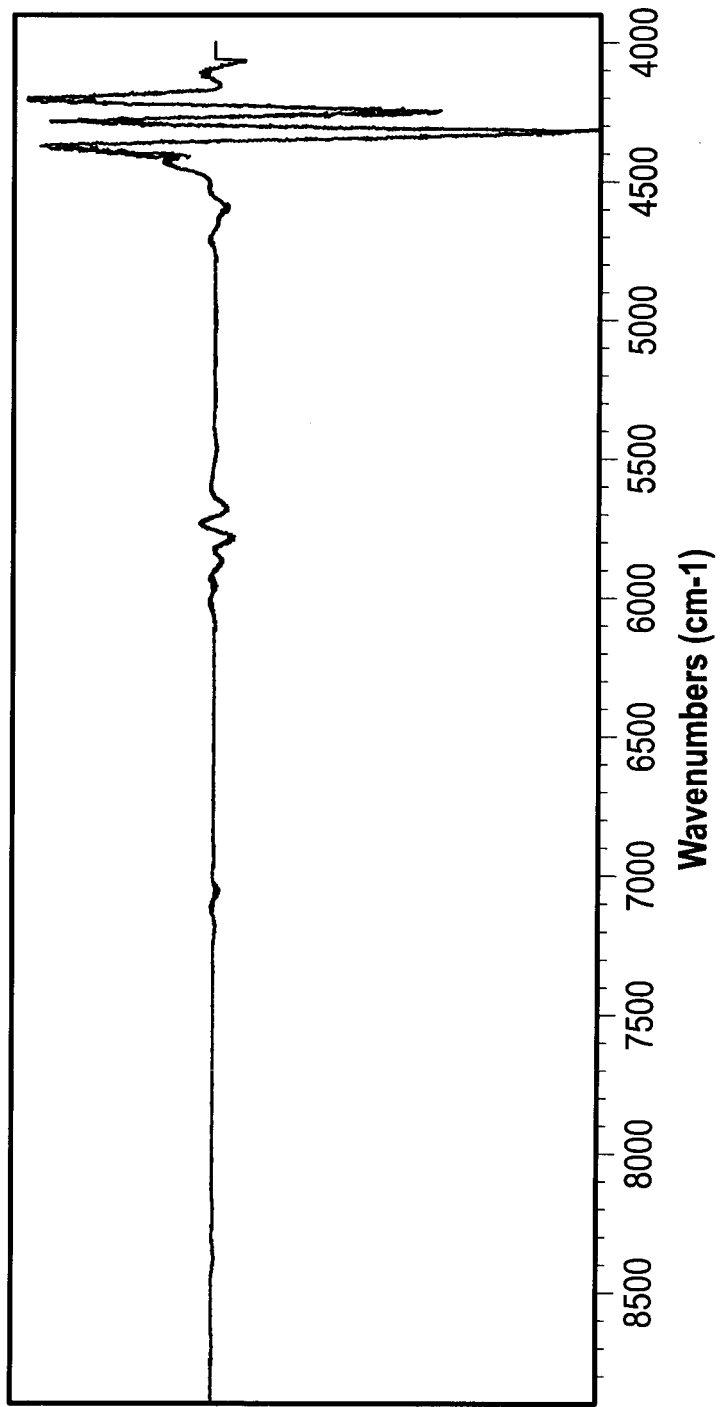
FIG. 3 illustrates a second derivative near-infrared spectra of a typical bio-oil prepared from the thermo-catalytic conversion of biomass which had been upgraded by hydrotreatment.
Figure 4:
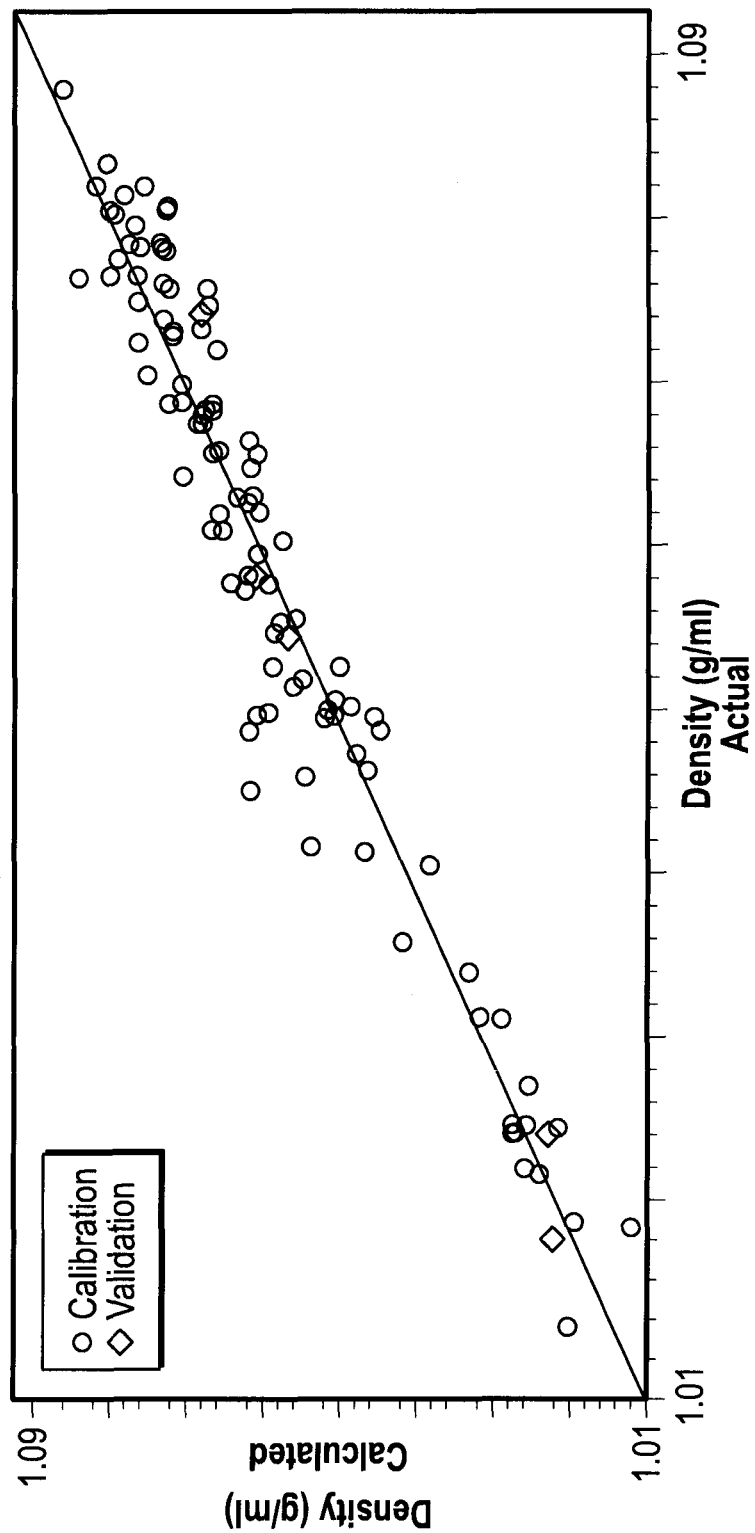
FIG. 4 is a calibration curve based on a correlation of measured density and NIR spectra for a plurality of bio-oils prepared from the thermo-catalytic conversion of biomass.
Figure 5:
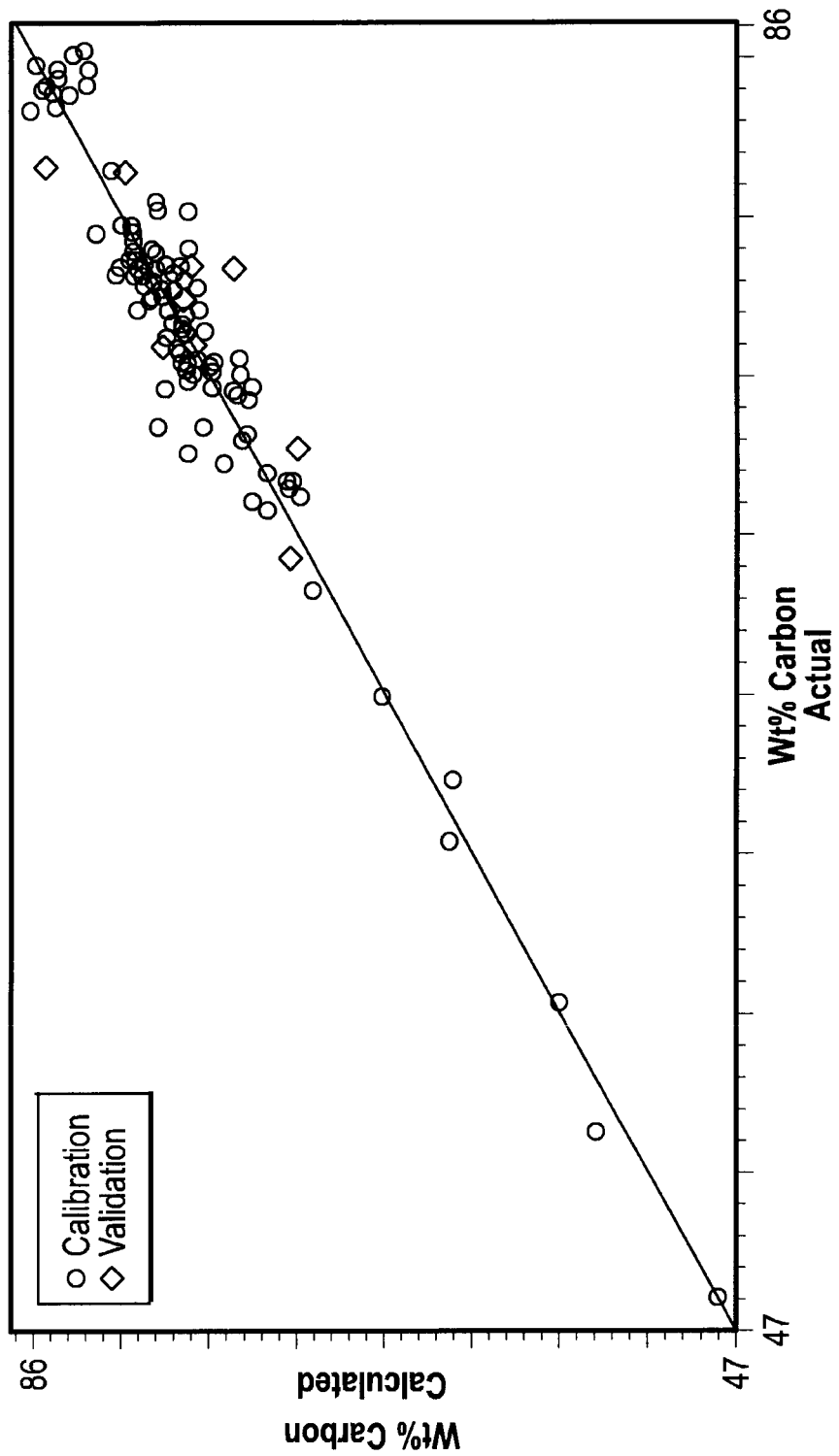
FIG. 5 is a calibration curve based on a correlation of measured wt % carbon and NIR spectra for a plurality of bio-oils prepared from the thermo-catalytic conversion of biomass.
Figure 6:
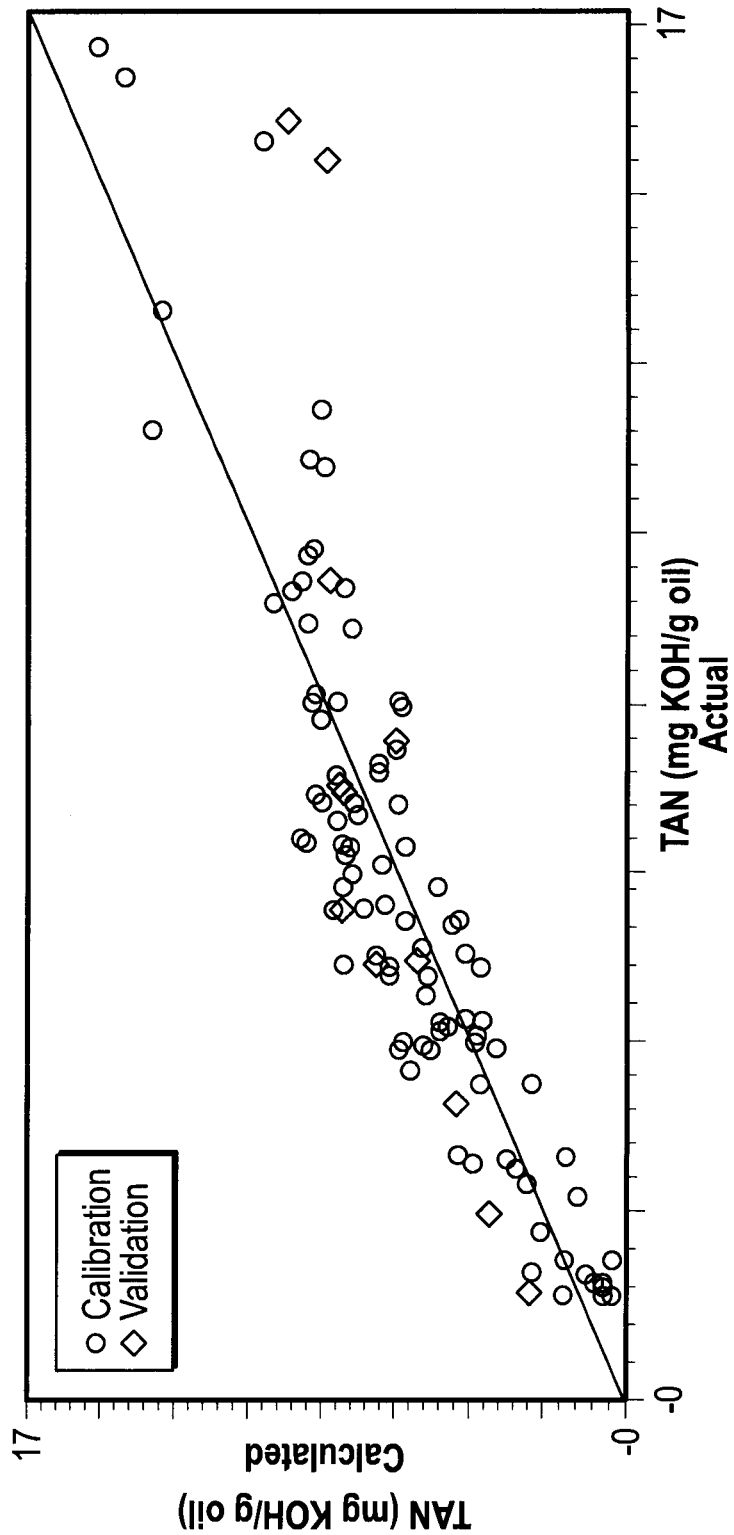
FIG. 6 is a calibration curve based on a correlation of measured TAN and NIR spectra for a plurality of bio-oils prepared from the thermo-catalytic conversion of biomass.
Figure 7:
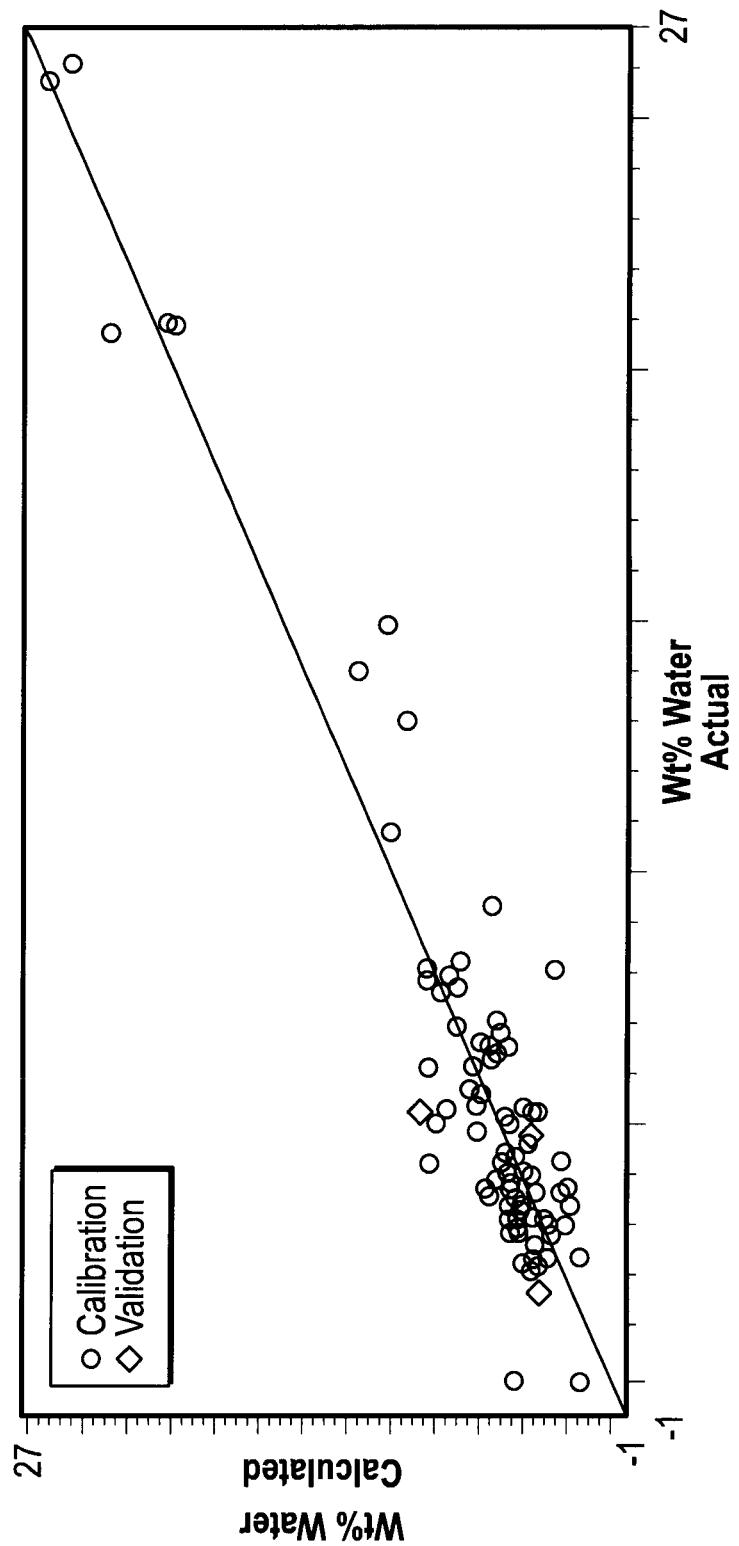
FIG. 7 is a calibration curve based on a correlation of measured wt % water and NIR spectra for a plurality of bio-oils prepared from the thermo-catalytic conversion of biomass.
Figure 8:
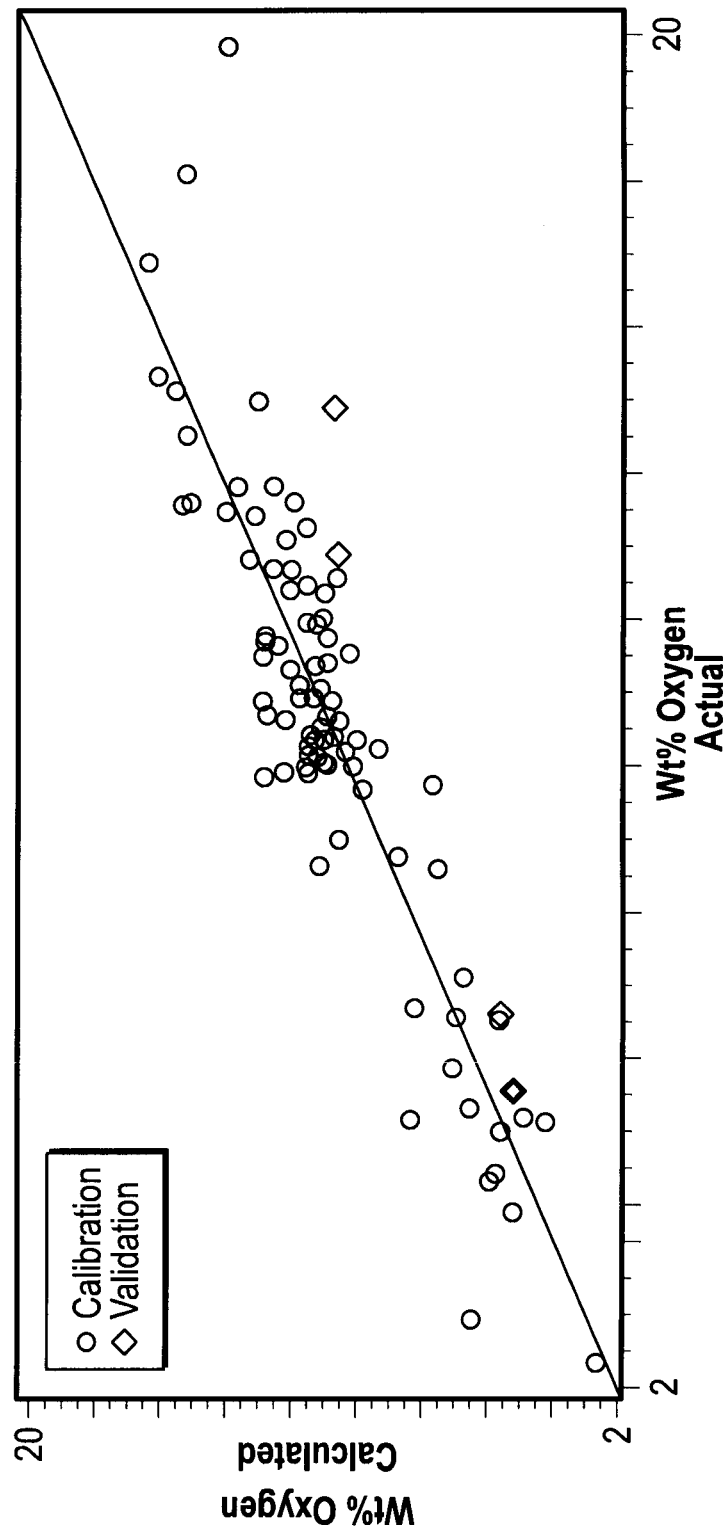
FIG. 8 is a calibration curve based on a correlation of measured wt % oxygen and NIR spectra for a plurality of bio-oils prepared from the therm-catalytic conversion of biomass.
Figure 9:
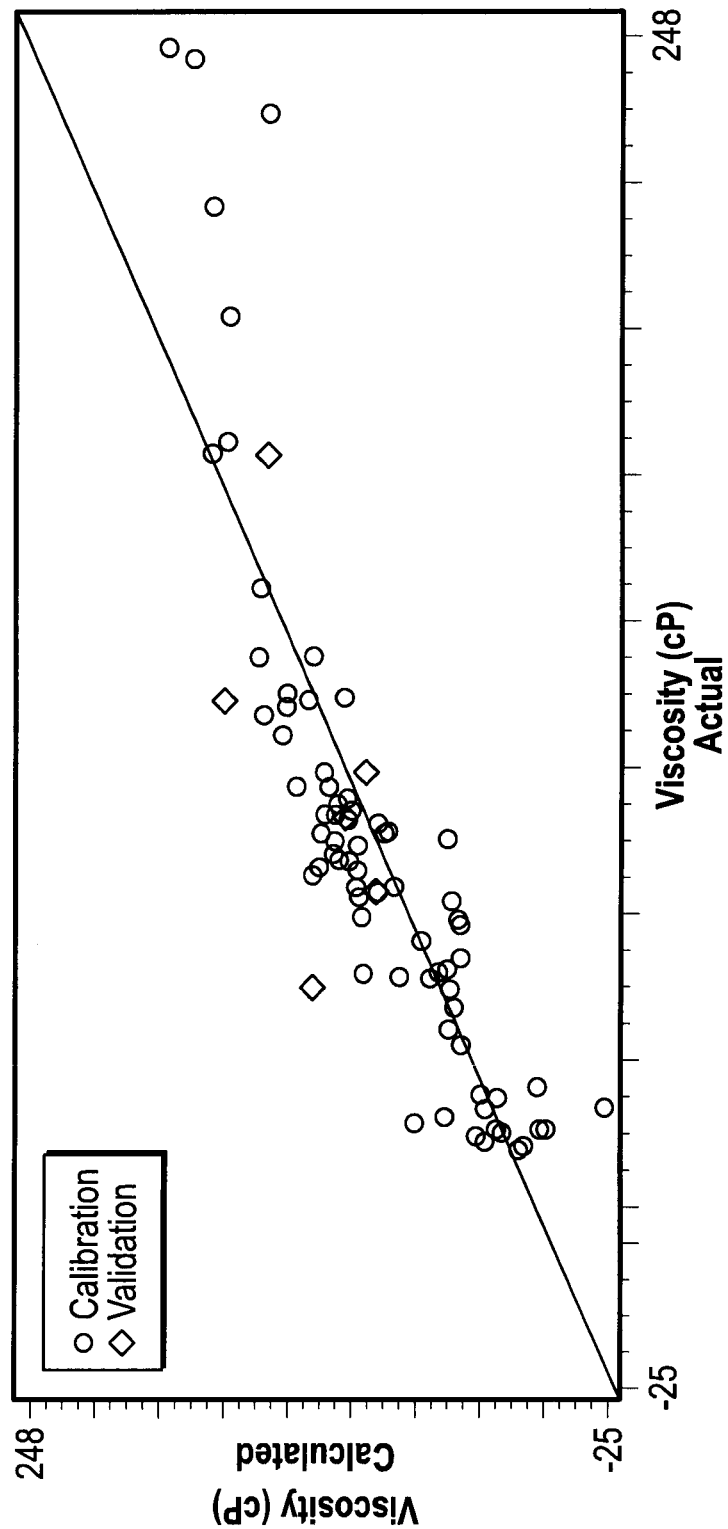
FIG. 9 is a calibration curve based on a correlation of measured viscosity and NIR spectra for a plurality of bio-oils prepared from the thermo-catalytic conversion of biomass.

FIG. 2 shows a second derivative near-infrared spectra of a typical raw bio-oil prepared from the thermo-catalytic conversion of southern yellow pine wood chips (having an oxygen content of around 15 wt %). FIG. 3 shows a second derivative near-infrared spectra of a sample of such bio-oil which has been deoxygenated by hydrotreatment (having an oxygen content less than around 0.5 wt %).

As can be seen in FIGS. 2 and 3, the second derivatives of the spectra of the raw bio-oil and the upgraded bio-oil were quite different, which was expected due to the much higher oxygen content, and lower carbon and hydrogen contents, of the raw bio-oil relative to the upgraded derivative thereof.

Example 1

Calibration Curves

Raw Bio-Oils

Spectra for this Example 1 were obtained using a Thermo Fisher FTNIR instrument which exhibited a standard deviation of wavelength position of less than 0.01 cm$^{-1}$ over a six month period of operation.

Numerous samples of raw bio-oils prepared from the thermo-catalytic conversion of southern yellow pine wood chips were subjected to testing for the following properties: density, wt % carbon, Total Acid Number (TAN), wt % water, wt % oxygen, and viscosity. FTNIR spectra were also acquired for all samples.

The calibration models/curves described below were obtained from the application of partial least squares to the FTNIR spectra and sample analyses.

Table 1 shows the correlation coefficient and the cross validation correlation coefficient for each of the raw bio-oil properties set out above. Also, Table 1 identifies which Figure illustrates the calibration curve for a particular property.

TABLE 1

| Property | Correlation Coefficient | Cross Validation Correlation Coefficient | FIG. |
|---|---|---|---|
| Density, g/ml | 0.967 | 0.86 | 4 |
| Wt % carbon | 0.975 | 0.85 | 5 |
| TAN, mg KOH/g oil | 0.911 | 0.82 | 6 |
| Wt % Water | 0.943 | 0.61 | 7 |
| Wt % Oxygen | 0.902 | 0.55 | 8 |
| Viscosity, cP | 0.871 | 0.736 | 9 |

As can be seen from Table 1, and FIGS. 4-9, the correlation coefficients are quite high, and most of the cross validation correlation coefficients show that the models are reasonably robust. Also, the data in Table 1, and FIGS. 4-9, show that useful correlations can be made between raw bio-oil properties and near-infrared spectra, allowing for good predictions of such properties for future raw bio-oil samples.

Example 2

Calibration Curves

De-Watered Bio-Oils

Spectra for this Example 2 were obtained using a Thermo Fisher FTNIR instrument which exhibited a standard deviation of wavelength position of less than 0.01 cm$^{-1}$ over a six month period of operation.

Bio-oils prepared from the thermo-catalytic conversion of southern yellow pine wood chips were de-watered. Such de-watering was by first "flipping" the layers of the bio-oil by altering the density of the organic phase through the addition of a bio-naphtha stream, such that the organic phase (bio-oil) settled on top of the aqueous phase. The flipped organic phase was then separated from the aqueous phase by gravity separation and decanting, and solid material present in the raw bio-oils was removed with the aqueous phase, resulting in a significant reduction of the solids content in the resulting organic phases. The thus acquired organic phases were then subjected to desalting, wherein additional water and solids were removed, forming de-watered bio-oils.

Numerous samples of such de-watered bio-oils were subjected to testing for wt % water by Karl Fischer titration. FTNIR spectra were also acquired for all samples.

The calibration model/curve described below was obtained from the application of partial least squares to the FTNIR spectra and sample analyses.

Figure 10:
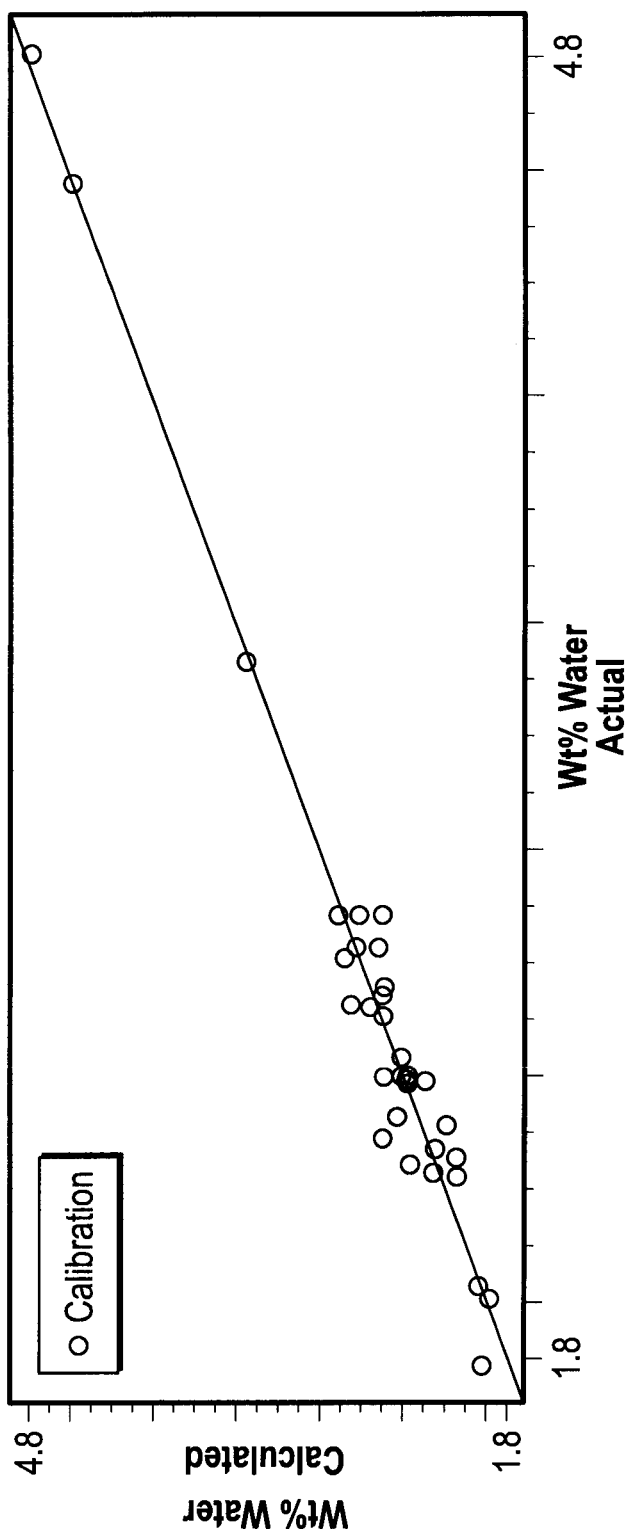
FIG. 10 is a calibration curve based on a correlation of measured wt % water and NIR spectra for a plurality of bio-oils prepared from the thermo-catalytic conversion of biomass, which had been flipped such that the bio-oil was on top of an aqueous phase, and which had subsequently been at least partially dewatered by decanting and desalting.

The correlation coefficient was 0.988, and the cross validation correlation coefficient was between 0.5 and 0.6. FIG. 10 illustrates the calibration curve for the wt % water property.

As can be seen from the data above and FIG. 10, the correlation coefficient is quite high. The cross validation correlation coefficient is relatively low due to too few calibration standards, but still sufficiently high to indicate the potential of the technique once additional standards are available for calibration. The model is useful in its current form for trend indication purposes in support of bio-oil de-watering processes.

Numerous samples of such de-watered bio-oils were subjected to testing for wt ppm solids by filtration. FTNIR spectra were also acquired for all samples.

The calibration model/curve described below was obtained from the application of partial least squares to the FTNIR spectra and sample analyses.

Figure 11:
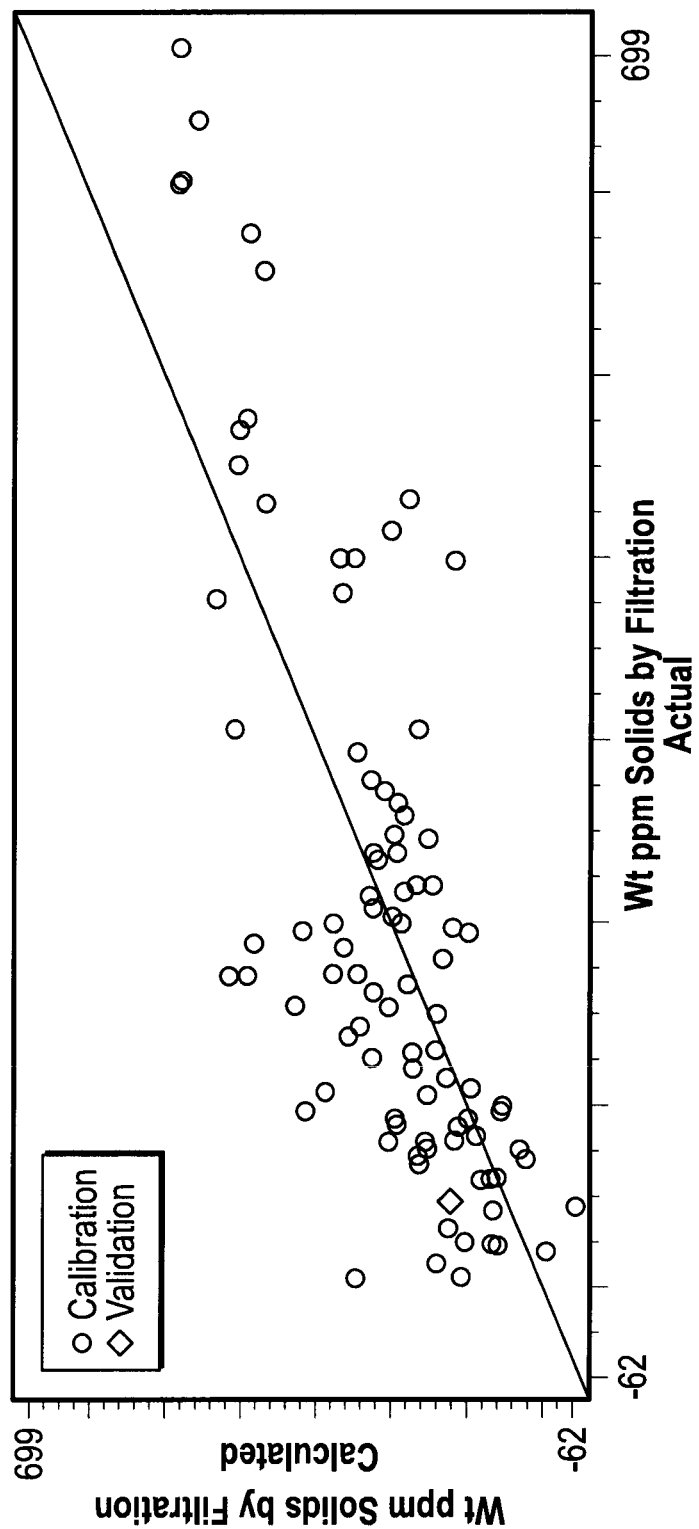
FIG. 11 is a calibration curve based on a correlation of measured wt ppm solids by filtration and NIR spectra for a plurality of bio-oils prepared from the thermo-catalytic conversion of biomass, which had been flipped such that the bio-oil was on top of an aqueous phase, and which had subsequently been at least partially dewatered by decanting and desalting.

The correlation coefficient was 0.744, and the cross validation correlation coefficient was 0.682. FIG. 11 illustrates the calibration curve for the wt ppm solids by filtration.

As can be seen from the data above and FIG. 11, the correlation coefficient is reasonably high. The cross validation correlation coefficient is relatively low due to too few calibration standards, but still sufficiently high to indicate the potential of the technique once additional standards are available for calibration. The model is useful in its current form for trend indication purposes in support of bio-oil de-watering processes.

Example 3

Calibration Curves

Upgraded Bio-Oils

Spectra for this Example 3 were obtained using a Thermo Fisher Antaris FTNIR instrument which exhibited a standard deviation of wavelength position of less than 0.01 cm$^{-1}$ over a six month period of operation.

Numerous samples of bio-oils prepared from the thermo-catalytic conversion of southern yellow pine wood chips, which were also deoxygenated by hydrotreatment, were subjected to testing for the following properties: wt % hydrogen and TAN. FTNIR spectra were also acquired for all samples.

The calibration models/curves described below were obtained from the application of partial least squares to the FTNIR spectra and sample analyses.

Table 2 shows the correlation coefficient and cross validation correlation coefficient for each of the upgraded bio-oil properties set out above. Also, Table 2 identifies which Figure illustrates the calibration curve for a particular property.

TABLE 2

| Property | Correlation Coefficient | Cross Validation Correlation Coefficient | FIG. |
|---|---|---|---|
| Wt % hydrogen | 0.973 | 0.8583 | 12 |
| TAN, mg KOH/g oil | 0.919 | 0.8096 | 13 |

Figure 12:
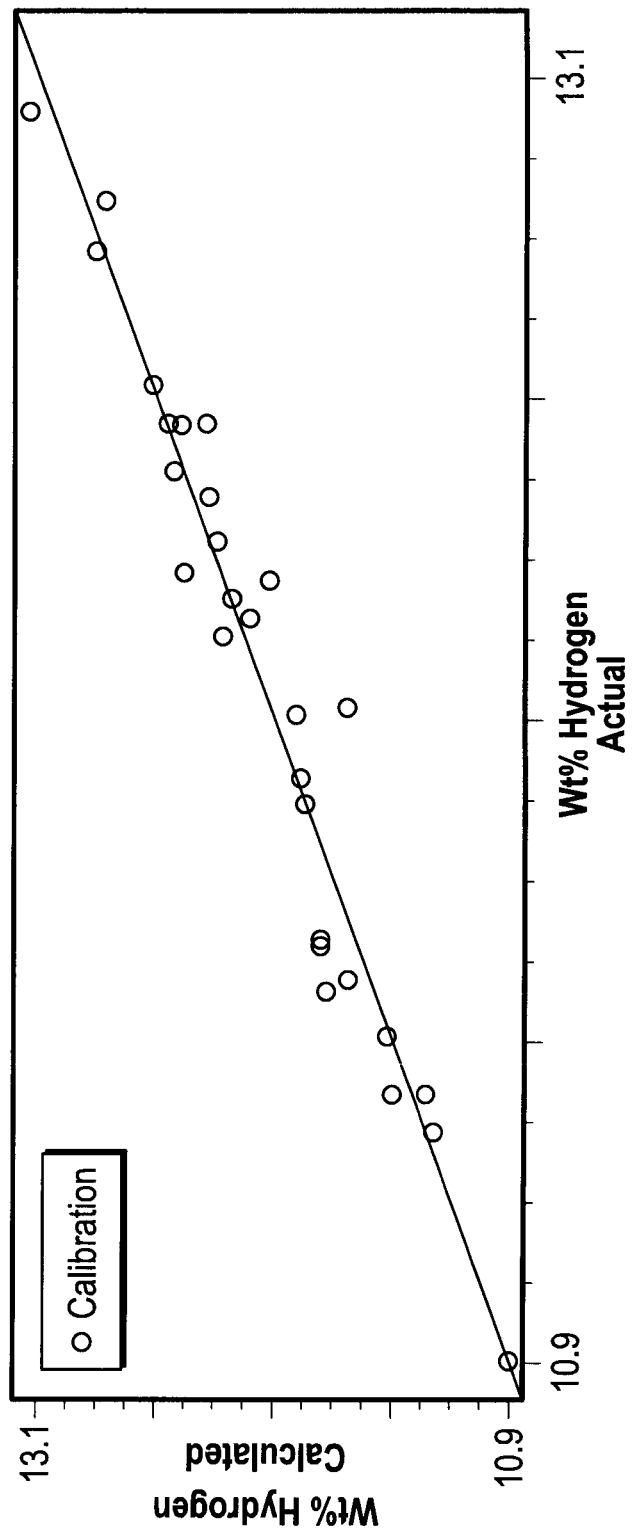
FIG. 12 is a calibration curve based on a correlation of measured wt % hydrogen and NIR spectra for a plurality of bio-oils prepared from the thermo-catalytic conversion of biomass, which had been upgraded by hydrotreatment.
Figure 13:
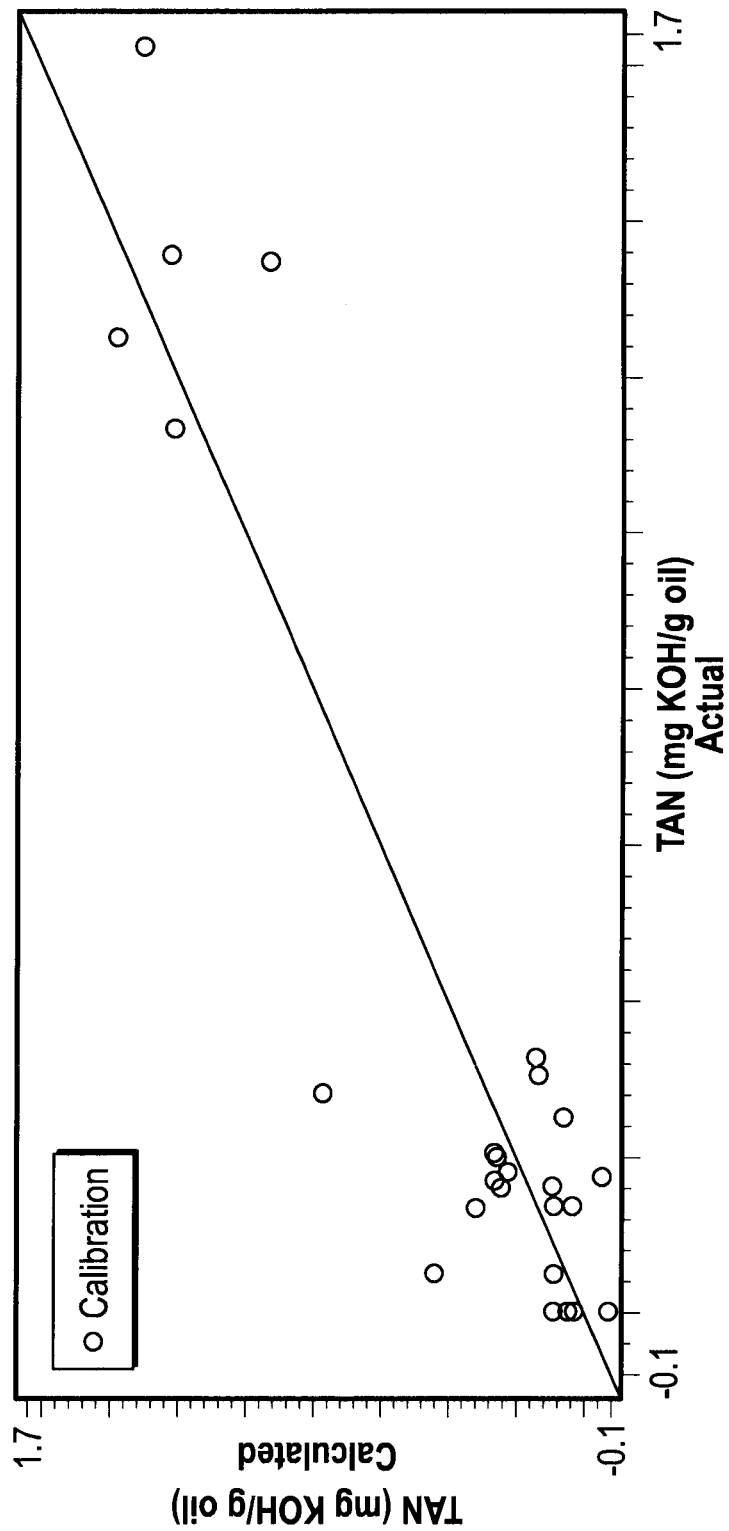
FIG. 13 is a calibration curve based on a correlation of measured TAN and NIR spectra for a plurality of bio-oils prepared from the thermo-catalytic conversion of biomass, which had been upgraded by hydrotreatment.

As can be seen from Table 2, and FIGS. 12-13, the correlation coefficients are quite high, and the cross validation correlation coefficients show that the models are reasonably robust. Also, the data in Table 2, and FIGS. 12-13, show that useful correlations can be made between upgraded bio-oil properties and near-infrared spectra, allowing for good predictions of such properties for future upgraded bio-oil samples.

Example 4

Calibration Curves

Gasoline/Bio-Naphtha Blends

Spectra for this Example 4 were obtained using a Thermo Fisher FTNIR instrument which exhibited a standard deviation of wavelength position of less than 0.01 cm$^{-1}$ over a six month period of operation.

Numerous samples of various blends of conventional gasoline and bio-naphtha fractions were subjected to testing for Motor Octane Number. The bio-naphtha fractions were fractions from a bio-oil prepared from the thermo-catalytic conversion of southern yellow pine wood chips which had been deoxygenated by hydrotreatment. FTNIR spectra were also acquired for all samples and for a sample of an 87 MON gasoline.

The calibration model/curve described below was obtained from the application of partial least squares to the FTNIR spectra and measured MON values for all samples.

Figure 14:
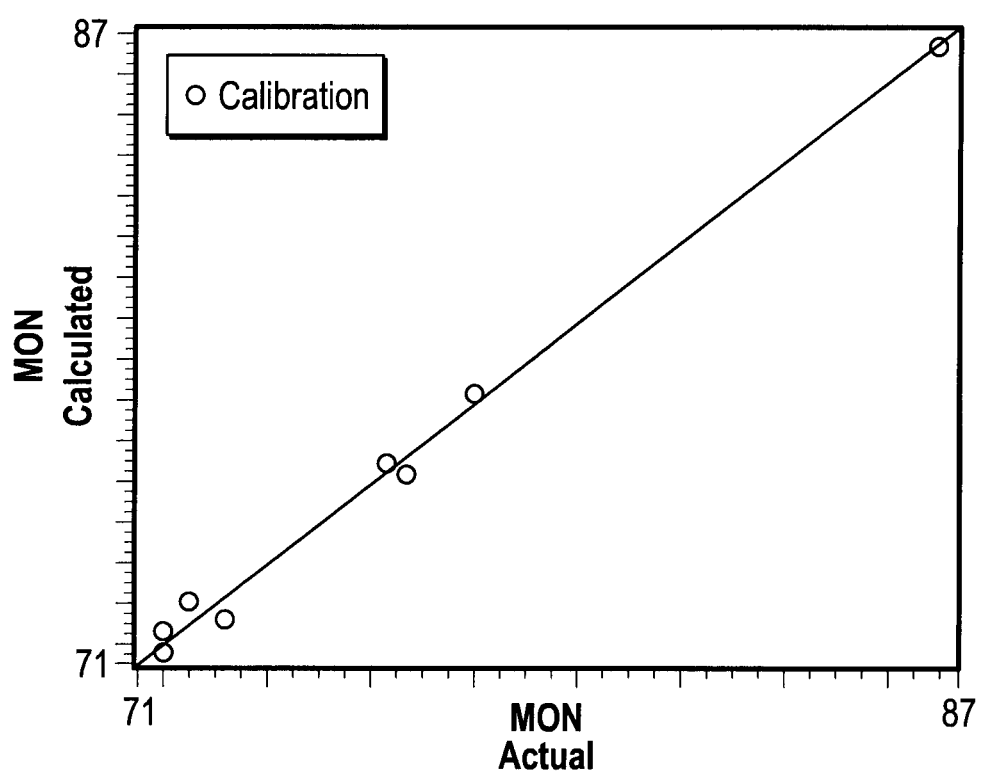
FIG. 14 is a calibration curve based on a correlation of measured MON values and NIR spectra for a plurality of model gasoline blends containing various amounts (including 0 wt %) of naphtha fractions from upgraded bio-oils prepared from the thermo-catalytic conversion of biomass.

The correlation coefficient was 0.997, and the cross validation correlation coefficient was >0.7. FIG. 14 illustrates the calibration curve for the MON property.

As can be seen from the data above and FIG. 14, the correlation coefficient is quite high, and the cross validation correlation coefficient is sufficiently high to show that the model is reasonably robust. Also, the data above and FIG. 14 show that, for blends of conventional gasoline and the bio-naphtha fractions of the present invention, useful correlations can be made between the measured MON and near-infrared spectra, allowing for good predictions of MON for future conventional gasoline/bio-naphtha fraction blends.

Example 5

Calibration Curves

Distillate/Bio-Distillate Blends

Spectra for this Example 5 were obtained using a Thermo Fisher FTNIR instrument which exhibited a standard deviation of wavelength position of less than 0.01 cm$^{-1}$ over a six month period of operation.

Numerous samples of various blends of conventional distillate and bio-distillate fractions were subjected to testing for cetane number. The bio-distillate fractions were fractions from a bio-oil prepared from the thermo-catalytic conversion of southern yellow pine wood chips which had been deoxygenated by hydrotreatment. FTNIR spectra were also acquired for all samples and for a sample of a commercial distillate.

The calibration model/curve described below was obtained from the application of partial least squares to the FTNIR spectra and measured cetane number values for all samples.

Figure 15:
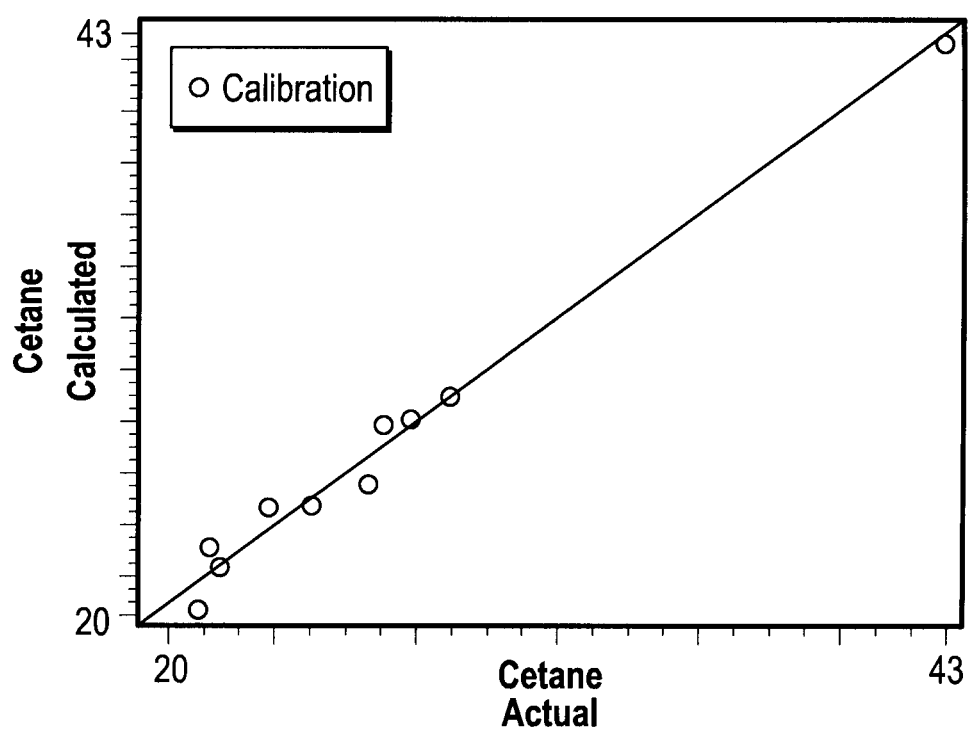
FIG. 15 is a calibration curve based on a correlation of measured cetane number values and NIR spectra for a plurality of model distillate blends containing various amounts (including 0 wt %) of distillate fractions from upgraded bio-oils prepared from the thermo-catalytic conversion of biomass.

The correlation coefficient was 0.993, and the cross validation correlation coefficient was 0.733. FIG. 15 illustrates the calibration curve for the cetane number property.

As can be seen from the data above and FIG. 15, the correlation coefficient is quite high, and the cross validation correlation coefficient is sufficiently high to indicate the potential of the technique to predict cetane number from near-infrared spectra once additional standards are available for calibration.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

Further, unless expressly stated otherwise, the term "about" as used herein is intended to include and take into account variations due to manufacturing tolerances and/or variabilities in process control.

Changes may be made in the construction and the operation of the various components, elements and assemblies described herein, and changes may be made in the steps or sequence of steps of the methods described herein without departing from the spirit and the scope of the invention as defined in the following claims.

What is claimed is:

1. A method for determining a property for a hydrocarbonaceous sample comprising a component prepared from the thermo-catalytic conversion of biomass at a temperature in the range of from about 200° C. to about 1000° C., and in the substantial absence of oxygen; said method comprising:
   a) measuring a model property for each of a plurality of model hydrocarbonaceous materials comprising varying amounts of said component;
   b) acquiring a plurality of model absorbances over a near-infrared spectrum for each of said model hydrocarbonaceous materials;
   c) correlating said model properties with said plurality of model absorbances to establish a correlation;
   d) acquiring a plurality of sample absorbances over said near-infrared spectrum for said hydrocarbonaceous sample; and
   e) comparing said plurality of sample absorbances to said plurality of model absorbances using said correlation to thereby determine said property for said hydrocarbonaceous sample.

2. The method of claim 1 wherein the standard deviation of the wavenumber shift between: 1) a first near-infrared instrument used to acquire an absorbance in steps b) or d), and 2) a second near-infrared instrument is less than about 0.02 wavenumbers.

3. The method of claim 1 wherein the standard deviation of the wavenumber shift between: 1) a first near-infrared instrument used to acquire an absorbance in steps b) or d), and 2) a second near-infrared instrument is less than about 0.01 wavenumbers.

4. The method of claim 3 wherein the standard deviation of the wavenumber shift is sufficient to allow calibration transfer from said first near-infrared instrument to said second near-infrared instrument, wherein the root mean square error of prediction for said second near-infrared instrument is less than or equal to the root mean square error of prediction for said first near-infrared instrument.

5. The method of claim 1 wherein said near infrared spectrum is sub-divided by wavelength into a plurality of groups, each separately defined by a wavelength range, and wherein each of the absorbances of: 1) said plurality of model absorbances, and 2) said plurality of sample absorbances is a total absorbance acquired over one of said wavelength ranges corresponding to one of said groups.

6. The method of claim 1 wherein a plurality of wavelengths are identified over said near infrared spectrum, and wherein each of the absorbances of: 1) said plurality of model absorbances, and 2) said plurality of sample absorbances is an absorbance acquired at one of said plurality of wavelengths.

7. The method of claim 1 wherein said hydrocarbonaceous sample, said component, and said plurality of model hydrocarbonaceous materials are transportation fuel-range fractions.

8. The method of claim 7 wherein said property is selected from the group consisting of Motor Octane Number, Research Octane Number, cetane number, and density.

9. A process comprising: a) blending said transportation fuel-range fraction from claim 8 with at least one petroleum-sourced fuel component, b) comparing the value of said property determined from said correlation of claim 8 with a desired set point value, and c) adjusting the ratio of said transportation fuel-range fraction to said at least one petroleum-sourced fuel component accordingly.

10. The method of claim 8 wherein said property is Motor Octane Number; said hydrocarbonaceous sample and said plurality of model hydrocarbonaceous materials have Motor Octane Numbers in the range of from about 70 to about 90; and the spectral range for said near-infrared spectrum is from about 4000 to about 10000 wavenumbers.

11. The method of claim 8 wherein said property is Research Octane Number; said hydrocarbonaceous sample and said plurality of model hydrocarbonaceous materials have Research Octane Numbers in the range of from about 70 to about 90; and the spectral range for said near-infrared spectrum is from about 4000 to about 10000 wavenumbers.

12. The method of claim 8 wherein said property is cetane number; said hydrocarbonaceous sample and said plurality of model hydrocarbonaceous materials have cetane numbers in the range of from about 20 to about 60; and the spectral range for said near-infrared spectrum is from about 4000 to about 10000 wavenumbers.

13. The method of claim 8 wherein said property is density; said hydrocarbonaceous sample and said plurality of model hydrocarbonaceous materials have densities in the range of from about 0.80 g/ml to about 0.91 g/ml; and the spectral range for said near-infrared spectrum is from about 4000 to about 10000 wavenumbers.

14. The method of claim 7 wherein said hydrocarbonaceous sample and said plurality of model hydrocarbonaceous materials further comprise petroleum-sourced fuel components.

15. The method of claim 14 wherein said hydrocarbonaceous sample and said plurality of model hydrocarbonaceous materials further comprise components selected or obtained from the group consisting of pyrolysis oil, liquefied biomass, hydropyrolysis oils, alcohol, triglyceride-based oil, and combinations thereof.

16. The method of claim 1 wherein said hydrocarbonaceous sample, said component, and said plurality of model hydrocarbonaceous materials are bio-oils prepared from the thermo-catalytic conversion of biomass at a temperature in the range of from about 200° C. to about 1000° C., and in the substantial absence of oxygen; wherein said bio-oils contain oxygen in the range of from about 1 wt % to about 50 wt % oxygen, measured on a dry basis.

17. The method of claim 1 wherein said hydrocarbonaceous sample, said component, and said plurality of model hydrocarbonaceous materials are bio-oils prepared from the thermo-catalytic conversion of biomass at a temperature in the range of from about 200° C. to about 1000° C., and in the substantial absence of oxygen; wherein said bio-oils contain oxygen in the range of from about 1 wt % to about 20 wt % oxygen, measured on a dry basis.

18. The method of claim 17 wherein said property is selected from the group consisting of wt % oxygen measured on a dry basis, viscosity, TAN, wt % water, wt % carbon, and density.

19. A process for producing a bio-oil by the thermo-catalytic conversion of biomass under bio-oil production conditions including a temperature in the range of from about 200° C. to about 1000° C., and in the substantial absence of oxygen, comprising: a) comparing the value of said property determined from said correlation of claim 18 with a desired set point value, and b) adjusting said bio-oil production conditions accordingly.

20. The method of claim 18 wherein said property is wt % oxygen measured on a dry basis; and the spectral range for said near-infrared spectrum is from about 4000 to about 10000 wavenumbers.

21. The method of claim 18 wherein said property is viscosity as measured at about 40° C.; said hydrocarbonaceous sample and said plurality of model hydrocarbonaceous materials have viscosities greater than 0 and up to about 1200 cP; and the spectral range for said near-infrared spectrum is from about 4400 to about 9200 wavenumbers.

22. The method of claim 18 wherein said property is TAN; said hydrocarbonaceous sample and said plurality of model hydrocarbonaceous materials have TAN values in the range of from about 0.05 to about 50 mg KOH/g oil; and the spectral range for said near-infrared spectrum is from about 4400 to about 9200 wavenumbers.

23. The method of claim 18 wherein said property is wt % water; said hydrocarbonaceous sample and said plurality of model hydrocarbonaceous materials have wt % water contents in the range of from about 0.2 to about 36 wt %; and the spectral range for said near-infrared spectrum is from about 4400 to about 10000 wavenumbers.

24. The method of claim 18 wherein said property is wt % carbon; said hydrocarbonaceous sample and said plurality of model hydrocarbonaceous materials have wt % carbon contents in the range of from about 70 to about 82 wt %; and the spectral range for said near-infrared spectrum is from about 4400 to about 9200 wavenumbers.

25. The method of claim 18 wherein said property is density; said hydrocarbonaceous sample and said plurality of model hydrocarbonaceous materials have densities in the range of from about 1 to about 1.2 g/ml; and the spectral range for said near-infrared spectrum is from about 4000 to about 10000 wavenumbers.

26. The method of claim 16 wherein said hydrocarbonaceous sample and said plurality of model hydrocarbonaceous materials contain or are selected from the group consisting of pyrolysis oil, liquefied biomass, hydropyrolysis oil, thermo-catalytic oil, and combinations thereof.

27. The method of claim 1 wherein said hydrocarbonaceous sample, said component, and said plurality of model hydrocarbonaceous materials are de-watered bio-oils derived from bio-oils prepared from the thermo-catalytic conversion of biomass at a temperature in the range of from about 200° C. to about 1000° C., and in the substantial absence of oxygen; wherein said bio-oils contain oxygen in the range of from about 1 wt % to about 50 wt % oxygen, measured on a dry basis; and wherein said bio-oils have been at least partially de-watered forming said de-watered bio-oils, wherein said property is selected from the group consisting of wt % water and wt ppm solids by filtration.

28. The method of claim 27 wherein, prior to said at least partial de-watering, said bio-oils comprise an organic phase and an aqueous phase, and wherein said at least partial de-watering of said bio-oils comprises: i) altering the density of either said organic phase or said aqueous phase, ii) allowing said organic phase to settle on top of said aqueous phase, iii) separating at least a portion of said organic phase from said aqueous phase forming a separated organic phase, iv) subjecting said separated organic phase to desalting to remove additional water and forming said de-watered bio-oils.

29. A process for at least partially de-watering a bio-oil prepared from the thermo-catalytic conversion of biomass at a temperature in the range of from about 200° C. to about 1000° C., and in the substantial absence of oxygen comprising: a) subjecting said bio-oil to a voltage differential in a desalter operated under desalting conditions, b) comparing the value of said property determined from said correlation of claim 27 with a desired set point value, and c) adjusting said voltage differential accordingly.

30. The method of claim 27 wherein said property is wt % water; said hydrocarbonaceous sample and said plurality of model hydrocarbonaceous materials have wt % water contents in the range of from about 0.5 to about 5 wt %; and the spectral range for said near-infrared spectrum is from about 4500 to about 10000 wavenumbers.

31. The method of claim 27 wherein said property is wt ppm solids by filtration; said hydrocarbonaceous sample and said plurality of model hydrocarbonaceous materials have wt ppm solids by filtration contents in the range of from about 100 to about 1500 wt ppm; and the spectral range for said near-infrared spectrum is from about 4500 to about 10000 wavenumbers.

32. The method of claim 27 wherein said hydrocarbonaceous sample and said plurality of model hydrocarbonaceous materials contain or are selected from the group consisting of pyrolysis oil, liquefied biomass, hydropyrolysis oil, thermo-catalytic oil, and combinations thereof.

33. The method of claim 1 wherein said hydrocarbonaceous sample, said component, and said plurality of model hydrocarbonaceous materials are bio-oils prepared from the thermo-catalytic conversion of biomass at a temperature in the range of from about 200° C. to about 1000° C., and in the substantial absence of oxygen; wherein said bio-oils are at least partially deoxygenated.

34. The method of claim 33 wherein said property is selected from the group consisting of wt % hydrogen and TAN.

35. A process for at least partially deoxygenating a bio-oil prepared from the thermo-catalytic conversion of biomass at a temperature in the range of from about 200° C. to about 1000° C., and in the substantial absence of oxygen comprising: a) contacting said bio-oil with a de-oxygenation catalyst under de-oxygenation conditions, b) comparing the value of said property determined from said correlation of claim 34 with a desired set point value, and c) adjusting said de-oxygenation conditions accordingly.

36. The method of claim 34 wherein said property is wt % hydrogen; said hydrocarbonaceous sample and said plurality of model hydrocarbonaceous materials have wt % hydrogen contents in the range of from about 10 to about 14 wt %; and the spectral range for said near-infrared spectrum is from about 4000 to about 10000 wavenumbers.

37. The method of claim 34 wherein said property is TAN; said hydrocarbonaceous sample and said plurality of model hydrocarbonaceous materials have TAN values greater than 0 and up to about 2 mg KOH/g oil; and the spectral range for said near-infrared spectrum is from about 4000 to about 10000 wavenumbers.

38. The method of claim 1 wherein said correlation has a correlation coefficient greater than about 0.7.

39. The method of claim 1 wherein the spectra used to acquire the absorbances are fourier transform near-infrared spectra.

40. The method of claim 39 wherein the correlation of said model properties with said model absorbances is by use of partial least squares.

* * * * *